United States Patent
Ferree

(10) Patent No.: US 7,048,764 B2
(45) Date of Patent: May 23, 2006

(54) ARTIFICIAL DISC REPLACEMENTS WITH ARTICULATING COMPONENTS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/752,729

(22) Filed: Jan. 7, 2004

(65) Prior Publication Data

US 2004/0138753 A1 Jul. 15, 2004

Related U.S. Application Data

(60) Provisional application No. 60/438,408, filed on Jan. 7, 2003.

(51) Int. Cl.
*A61F 2/44* (2006.01)
(52) U.S. Cl. .................. 623/17.15; 623/17.16
(58) Field of Classification Search ............ 623/16.11, 623/17.11, 17.12, 17.13, 17.14, 17.15, 17.16, 623/18.11; 606/61
See application file for complete search history.

(56) References Cited

U.S. PATENT DOCUMENTS

| | | | | |
|---|---|---|---|---|
| 4,759,766 A | * | 7/1988 | Buettner-Janz et al. | 623/17.15 |
| 5,314,477 A | * | 5/1994 | Marnay | 623/17.15 |
| 5,401,269 A | * | 3/1995 | Buttner-Janz et al. | 623/17.15 |
| 5,534,029 A | * | 7/1996 | Shima | 623/17.15 |
| 5,674,296 A | * | 10/1997 | Bryan et al. | 623/17.16 |
| 5,676,701 A | * | 10/1997 | Yuan et al. | 623/17.15 |
| 5,888,226 A | * | 3/1999 | Rogozinski | 623/17.16 |
| 5,895,428 A | * | 4/1999 | Berry | 623/17.15 |
| 5,899,941 A | * | 5/1999 | Nishijima et al. | 623/17.15 |
| 6,063,121 A | * | 5/2000 | Xavier et al. | 623/17.15 |
| 6,146,421 A | * | 11/2000 | Gordon et al. | 623/17.15 |
| 6,368,350 B1 | * | 4/2002 | Erickson et al. | 623/17.14 |
| 6,540,785 B1 | * | 4/2003 | Gill et al. | 623/17.14 |
| 6,645,248 B1 | * | 11/2003 | Casutt | 623/17.12 |

* cited by examiner

Primary Examiner—Eduardo C. Robert
Assistant Examiner—David Comstock
(74) Attorney, Agent, or Firm—Gifford, Krass, Groh, Sprinkle, Anderson & Citkowski, PC

(57) ABSTRACT

Artificial disc replacements (ADRs) use articulating components to permit normal spinal movement(s). According to the invention, an ADR situated between upper and lower vertebral bodies comprises a first endplate affixed to one of the vertebral bodies providing a first articulating surface having a first radius of curvature, a second endplate affixed to the other one of the vertebral bodies providing a second articulating surface having a second radius of curvature which is different from the first radius of curvature, and a spacer component having opposing surfaces that cooperate with the first and second articulating surfaces. In the preferred embodiment, the first endplate is affixed to the upper vertebral body, the first articulating surface is concave, the second endplate is affixed to the lower vertebral body, the second articulating surface is convex, and the first radius of curvature is larger than the second radius of curvature. The spacer may include a surface that congruently cooperates with the first and/or articulating surface(s).

3 Claims, 1 Drawing Sheet

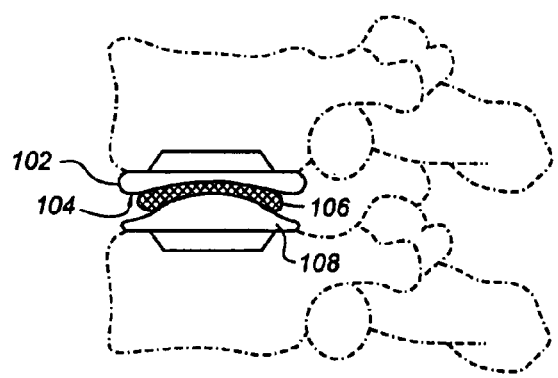
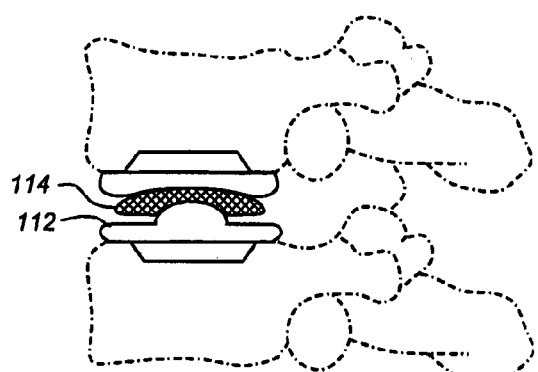
Fig - 1A
Fig - 1B
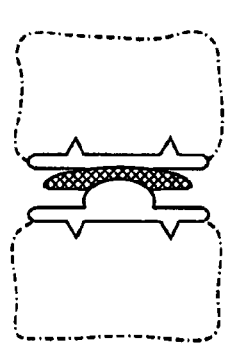
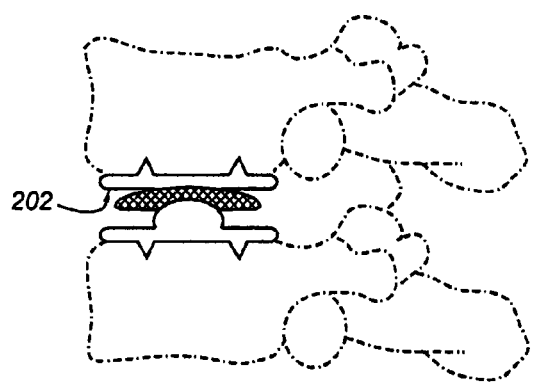
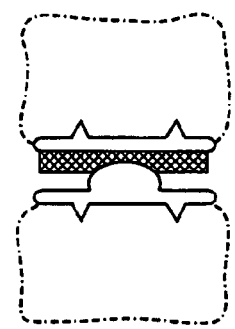
Fig - 1C
Fig - 2
Fig - 3
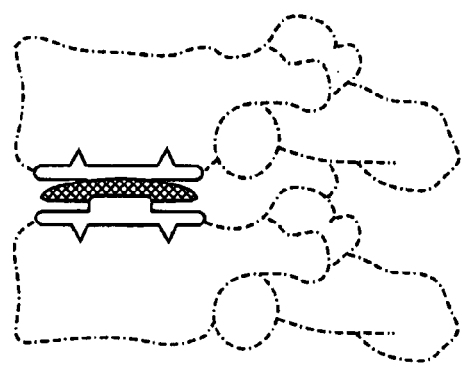
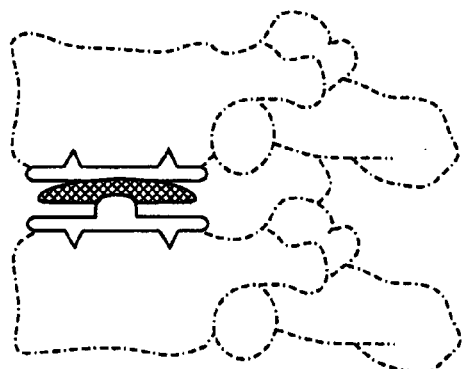
Fig - 4A
Fig - 4B

US 7,048,764 B2

ARTIFICIAL DISC REPLACEMENTS WITH ARTICULATING COMPONENTS

REFERENCE TO RELATED APPLICATION

This application claims priority from U.S. Provisional Patent Application Ser. No. 60/438,408, filed Jan. 7, 2003, the entire content of which is incorporated herein by reference.

FIELD OF THE INVENTION

This invention relates generally to artificial disc replacements (ADRs) and, in particular, to ADRs with articulating surfaces with various configurations to facilitate more normal spinal movements.

BACKGROUND OF THE INVENTION

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category. A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants, however, either replace the nucleus or the nucleus and the annulus. Both types of current procedures remove the degenerated disc component to allow room for the prosthetic component. Although the use of resilient materials has been proposed, the need remains for further improvements in the way in which prosthetic components are incorporated into the disc space, and in materials to ensure strength and longevity. Such improvements are necessary, since the prosthesis may be subjected to 100,000,000 compression cycles over the life of the implant.

One of the most important features of an artificial disc replacement (ADR) is its ability to replicate the kinematics of a natural disc. ADRs that replicate the kinematics of a normal disc are less likely to transfer additional forces above and below the replaced disc. In addition, ADRs with natural kinematics are less likely to stress the facet joints and the annulus fibrosus (AF) at the level of the disc replacement. Replicating the movements of the natural disc also decreases the risk of separation of the ADR from the vertebrae above and below the ADR.

SUMMARY OF THE INVENTION

In broad and general terms, this invention resides in artificial disc replacements (ADRs) which, in the preferred embodiments, use articulating components to permit normal spinal movement(s). According to the invention, an ADR situated between upper and lower vertebral bodies comprises a first endplate affixed to one of the vertebral bodies providing a first articulating surface having a first radius of curvature, a second endplate affixed to the other one of the vertebral bodies providing a second articulating surface having a second radius of curvature which is different from the first radius of curvature, and a spacer component having opposing surfaces that cooperate with the first and second articulating surfaces.

Though various materials may be used, biocompatible metals and/or ceramics are preferably used, and least for the endplates. While metals and/or ceramics may also be used for the spacer, a somewhat more wear resistant and resilient material such as polyethylene may be desirable. In any case, the invention is not limited in terms of material composition.

In the preferred embodiment, the first endplate is affixed to the upper vertebral body, the first articulating surface is concave, the second endplate is affixed to the lower vertebral body, the second articulating surface is convex, and the first radius of curvature is larger than the second radius of curvature. The spacer may include a surface that congruently cooperates with the first and/or articulating surface(s).

BRIEF DESCRIPTION OF THE DRAWINGS

FIG. 1A is a sagittal cross-section of the spine and an artificial disc replacement (ADR) according to the present invention;

FIG. 1B is a sagittal cross section of the spine and another ADR embodiment;

FIG. 1C is a coronal cross-section of the ADR of FIG. 1 relative to the spine;

FIG. 2 is a sagittal cross-section of an alternative embodiment including an ADR with a differently shaped endplate surface that may be non-congruent with the superior surface of the spacer;

FIG. 3 is a coronal cross-section of further alternative embodiment of the invention;

FIG. 4A is a coronal cross-section of yet a different alternative embodiment; and FIG. 4B is a sagittal cross-section of the ADR of FIG. 4A relative to the spine.

DETAILED DESCRIPTION OF THE INVENTION

FIG. 1A is a sagittal cross section of the spine and an artificial disc replacement (ADR) constructed in accordance with the invention. The superior ADR endplate (EP) 102 has a concave articulating surface 104 that cooperates with a spacer component 106. The spacer component 106 also articulates with the inferior ADR EP 108. Note that, in this embodiment, the concave and convex articulating surfaces between the three components are congruent. The surfaces are also preferably spherical. In addition, the superior articulating surface of the spacer component has a different radius of curvature than the inferior articulating surface of the spacer component.

FIG. 1B is a sagittal cross section of the spine and another embodiment of the invention, wherein the articulating surfaces between the inferior ADR EP 112 and the spacer component 114 have a smaller radii. Components with smaller radii allow more spinal flexion, extension, and lateral bending with less translation than the components with larger radii allow. FIG. 1C is a coronal cross section of the ADR drawn in FIG. 1 and the spine.

FIG. 2 is a sagittal cross-section of an alternative embodiment including an ADR with a differently shaped endplate surface 202 that may be non-congruent with the superior surface of the spacer. FIG. 3 is a coronal cross section of an alternative embodiment similar to the ADR drawn in FIG. 2, but wherein the superior surface of the articulating component with the socket is convex when viewed from the lateral side and flat when viewed from the front.

FIG. 4A is a coronal cross section of an alternative embodiment of the device and the spine. In this case the projection from the inferior ADR endplate has a substantially straight shape when viewed from the front. Lateral bending of the spine is achieved by sliding and tilting of the superior ADR endplate. FIG. 4B is a sagittal cross section of the ADR drawn in FIG. 4A and the spine. In this case the projection from the inferior ADR endplate has a circular shape when viewed from the lateral side. Flexion and extension of the spine is achieved by tilting of the hemispherical component and tilting and sliding of the ADR endplate.

I claim:

1. An artificial disc replacement (ADR) situated between immediately adjacent upper and lower vertebral bodies to facilitate multidimensional spinal movement, comprising:
   a spacer component having a spherical convex articulating surface and a spherical concave articulating surface; and
   a first endplate component adapted for fixation to an endplate of a vertebral body facing into an intervertebral disc space, the first endplate component including a spherical concave articulating surface having a first radius or curvature that congruently cooperates with the spherical convex articulating surface of the spacer component; and
   a second endplate component adapted for fixation to an endplate of an opposing vertebral body facing into the same intervertebral disc space, the second endplate component including a spherical convex articulating surface having a second radius of curvature that congruently cooperates with the spherical concave articulating surface of the spacer component.

2. The ADR of claim 1, wherein the first and second radii of curvature are different.

3. The ADR of claim 1, wherein:
   the first endplate component is affixed to the inferior endplate of an upper vertebral body;
   the second endplate component is affixed to the superior endplate of a lower vertebral body; and
   the first radius of curvature is larger than the second radius of curvature.

* * * * *